United States Patent
Rademacher et al.

(10) Patent No.: US 6,369,003 B1
(45) Date of Patent: Apr. 9, 2002

(54) PROCESS AND COMPOSITION FOR SOIL IMPROVEMENT BY REDUCING MICROBIALLY FORMED ETHYLENE IN THE SOIL

(75) Inventors: Wilhelm Rademacher, Limburgerhof; Helmut Walter, Obrigheim; Eberhard Peter Schott, Neustadt, all of (DE); Dale R. Carlson, Hillsborough, NC (US); Lisa P. Schell, Raleigh, NC (US); Charles W. Helpert, Durham, NC (US); David E. Millhouse, Visalia; William M. Fletcher, Woodlake, both of CA (US); Hans J. von Amsberg, Chapel Hill, NC (US); Matthias Bratz, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/266,264

(22) Filed: Jun. 27, 1994

(51) Int. Cl.$^7$ .............................................. A01N 37/52
(52) U.S. Cl. ....................................... 504/319; 504/320
(58) Field of Search ................................. 504/319, 320

(56) References Cited

U.S. PATENT DOCUMENTS 4,744,811 A 5/1988 Schulz et al. .................. 71/86
5,364,834 A * 11/1994 Kirchner et al. ............ 504/319

FOREIGN PATENT DOCUMENTS

EP 501326 9/1992

OTHER PUBLICATIONS

Leshem et al., "Buckminsterfullerene ($C_{60}$ buckyball) inhibition of ethylene . . . ", 1993, *Current Plant Science and Biotechnology in Agriculture*, vol. 16, pp. 174–181.
Fearn et al., 1991, *Plant Physiol.*, vol. 96, p. 239–244.
Fukuda et al., *The Plant Hormone Ethylene*, 1991, pp. 279–292.
Guinel et al., 1992, *Plant Physiol.*, vol. 99, pp. 515–518.
Jackson et al., *The Plant Hormone Ethylene*, 1991, pp. 159–182.
Lee et al., 1992, *Plant Physiol.*, vol. 100, pp. 1334–1338.
Lee et al., 1992, *Plant Physiol.*, vol. 100, pp. 1759–1763.
Peters et al., 1989, *Plant Physiol.*, vol. 91, pp. 690–693.
Pirrung et al., *J. Chem. Society*, 1989, pp. 857–859.
Romani et al., *J. Plant Growth Regulation*, 1989, vol. 8, pp. 63–69.
Sakota et al., Abstract of JP–05199835.
Siefert et al., *Planta*, 1994, vol. 192, pp. 431–440.
Zaat et al., *Planta*, 1989, vol. 177, pp. 141–150.

* cited by examiner

Primary Examiner—S. Mark Clardy
(74) Attorney, Agent, or Firm—Keil & Weinkauf (57) ABSTRACT

A process for improvement of the soil by reducing microbially formed ethylene in the soil by bringing compounds which bind ethylene or of which it is known that they inhibit ethylene biosynthesis between S-adenosyl-L-methionine and 1-aminocyclopropane-carboxylic acid or 1-aminocyclopropane-1-carboxylic acid and ethylene respectively, into the soil zone relevant for the root growth of higher plants and allowing them to act there on the soil microorganisms.

2 Claims, 2 Drawing Sheets

PROCESS AND COMPOSITION FOR SOIL IMPROVEMENT BY REDUCING MICROBIALLY FORMED ETHYLENE IN THE SOIL

The present invention relates to a process for soil improvement and a process for increasing the assimilation of nitrogen by higher plants. The invention further relates to a composition for soil improvement and thus indirectly for promoting the yield capacity of higher plants, in particular crop plants, taking particular account of legumes.

As is known, the plant hormone ethylene gives rise in crop plants and other higher plants to a number of reactions which, based on agricultural and horticultural practice and on the storage and transport of plant products, in some cases have a positive effect and in some cases an adverse effect. It is therefore common practice to make controlled interventions in the processes which can be influenced by ethylene using suitable active compounds. To differentiate, there are essentially the following possibilities here:

1. Increasing the ethylene level in the tissue of the plants by
1.1 treating with ethylene or acetylene, which often has a similar effect to ethylene;
1.2 treating with ethylene-releasing compounds, eg. ethephon (active compound 1.2), etacelasil (see "The Pesticide Manual", 9th edition, No. 5680 and 5640),
1.3 treating with compounds from which ethylene is released by plant metabolism, eg. 1-aminocyclopropane-1-carboxylic acid;
1.4 treating with ethylene-inducing compounds, eg. 2,4-dichlorophenoxyacetic acid in the case of tomatoes.
2. Reducing the ethylene concentrations occurring in the plant tissue by
2.1 decomposing the ethylene present in the surrounding atmosphere (eg. by $KMnO_4$);
2.2 adsorbing the ethylene occurring in the surrounding atmosphere or in the plant [eg. by Buckminsterfullerene (Leshem et al., 1993, Buckminsterfullerenes ($C_{60}$ buckyball) inhibition of ethylene release from senescing legume foliage and cut carnations, Current Plant Science and Biotechnology in Agriculture 16: 174–181) or polymers of vinylquinoline (Sakota et al., 1993, Ethylene formation inhibitors containing vinylquinoline polymers, JP 05,199, 835)]
2.3 inhibitors of plant ethylene biosynthesis. The following groups are to be differentiated here with respect to their suspected intervention in ethylene biosynthesis:
2.3.1 inhibitors of the conversion of S-adenosyl-L-methionine to 1-aminocyclopropane-1-carboxylic acid, such as
  derivatives of vinylglycine [inter alia rhizobitoxin, aminoethoxyvinylglycine (active compound 2.3.1.1)]
  hydroxylamine derivatives [inter alia L-canaline, aminooxyacetic acid (active compound 2.3.1.2)]
  oxime ether derivatives eg. such as mentioned in EP-A 0 243 834 (= U.S. Pat. No. 4,744,811) or EP-A 501 326;
2.3.2 inhibitors of the conversion of 1-aminocyclopropane-1-carboxylic acid to ethylene such as
  $Co^{++}$ and $Ni^{++}$ ions
  decouplers of oxidative phosphorylation, eg. 2,4-dinitrophenol
  nonionic detergents based on polyoxyethylenesorbitan monolaurate (eg. Tween® 20=active compound 2.3.2.1), alkylphenoxypolyethoxyethanol (eg. Triton® X-100=active compound 2.3.2.2), synthetic fatty alcohols (eg. Lutensol® AO 10=active compound 2.3.2.3) or sodium dodecyl sulfate (=active compound 2.3.2.4)
  free radical scavengers such as n-propyl gallate
  polyamines such as putrescine (=tetramethylenediamine, active compound 2.3.2.5) and derivatives derived therefrom such as spermine ($NH_2(CH_2)_3NH(CH_2)_4NH(CH_2)_3$—$NH_2$, active compound 2.3.2.6) or spermidine (mono-γ-aminopropylputrescine, active compound 2.3.2.7)
  structural analogs to 1-aminocyclopropane-1-carboxylic acid such as α-aminoisobutyric acid (active compound 2.3.2.8) or 1-aminocyclopropene-1-carboxylic acid (Pirrung and Trinks, 1989, Ethylene biosynthesis. Aminocyclopropenecarboxylic acid, Journal of the Chemical Society, Chemical Communications, 857–859)
  salicylic acid (active compound 2.3.2.9) (Romani et al., 1989, Salicylic acid inhibition of ethylene production by apple discs and other plant tissues, Plant Growth Regulation 8: 63–69)
  inhibitors of cytochrome P-450-dependent monooxygenases [eg. tetcyclacis (active compound 2.3.2.10), 1-phenoxy-3-azol-1-yl-4-hydroxy-5,5-dimethylhexane (active compound 2.3.2.11), epoxyconazole (2RS,3RS-1-[3-2-chlorophenyl)-2-(4-fluorophenyl)-oxiran-2-ylmethyl]-1H-1,2,4-triazole, (active compound 2.3.2.12) (Siefert et al., 1994, Are ethylene and 1-aminocyclopropane-1-carboxylic acid involved in the induction of chitinase and β-1,3-glucanase activity in sunflower cell suspension cultures?, Planta 192: 431–440)
3. Inhibition of ethylene action by substances which block the site of reaction (ethylene receptor):
Examples known here are $CO_2$, silver ions, 2,5-norbornadiene, 3-amino-1,2,4-triazole and cis-propenylphosphonic acid.

As far as can be taken from the literature, the processes mentioned in 2.1 and 2.2 are employed mainly in storage rooms, eg. for fruit, vegetables or cut flowers. The processes indicated in 2.3 on the other hand comprise a plant treatment and are aimed at an immediate change of the ethylene status in the tissue of the higher plant. Methods to reduce the ethylene content in the soil, ie. in the soil atmosphere, however, are unknown in practice.

Its an object of the present invention to find processes by which the soil in the root area of plants can be improved and by which, as a result, the growth and/or the assimilation of $N_2$ from the air by higher plants can be increased. The achievement of this object should in the end result in causing a higher yield capacity of crop plants, in particular of legumes such as eg. beans, peas, lucerne, groundnuts, soybeans etc.

We have found that this object is achieved by a process for soil improvement which comprises carrying out a reduction of microbially produced ethylene in the soil by bringing compounds which bind ethylene or inhibit ethylene biosynthesis in higher plants between S-adenosyl-L-methionine and 1-aminocyclopropanecarboxylic acid or 1-aminocyclopropane-1-carboxylic acid and ethylene respectively into the soil zone relevant for the root growth of higher plants and allowing them to act there on the soil microorganisms.

A process for increasing the assimilation of nitrogen by higher plants has furthermore been found, which comprises adding to the soil zone relevant for root growth compounds which bind ethylene or in higher plants inhibit ethylene biosynthesis between S-adenosyl-L-methionine and 1-aminocyclopropane-1-carboxylic acid or 1-aminocyclopropanecarboxylic acid and ethylene respectively.

The invention further relates to compositions for soil improvement, by reducing microbially produced ethylene in the soil, which contain compounds of the abovementioned groups or mixtures thereof and the use of these compositions for soil improvement.

Increased ethylene concentrations in the soil lead in most crop plants to reduced growth and thus to depressed yields. Only rice and a few other plants suited to growth in wet soils or in water react in a less sensitive manner in this respect.

Inhibition of root growth is only to be expected according to M. B. Jackson, Ethylene in root growth and development, in: The Plant Hormone Ethylene, Mattoo, A. K. and Suttle, J. C. (eds.), CRC Press, Boca Raton, 1991, pp. 159–182, when in stress situations excessive ethylene formation by the root tissue occurs or when the endogenously formed ethylene accumulates as a result of reduced gas exchange in the area of the roots. Under field conditions, adverse effects on root growth of this type can occur when the gas exchange of the soil is inadequate—eg. as a result of severe wetness. On the one hand, the ethylene formed by the root itself can then accumulate, but on the other hand under these conditions there is the risk that concentration of microbially produced ethylene can occur.

Ethylene can be of particularly adverse significance in the growth and in the formation of yield of legumes. The plant species belonging to the order of the legumes (Fabales) are able to fix atmospehric nitrogen ($N_2$) by the symbiosis taking place in special organs of the root (root nodules) using bacteria of the genera Rhizobium or Bradyrhizobium and thus to make it accessible for the growth of the higher plants. The process of root nodule formation (nodulation) is obviously inhibited by ethylene in the root area. On the other hand, it is possible in isolated cases to promote nodulation in mutants having reduced or deficient nodulation if ethylene antagonists are employed. In this respect eg. the following reports are available from laboratory investigations.

In the case of the mutant EZ (Sym5) of peas (*Pisum sativum*), the severely reduced nodule formation can be partially restored by aminoethoxyvinylglycine (2.3.1.1), $Co(NO_3)_2$ and $Ag_2SO_4$. The nodulation of the parent strain Sparkle is not affected, however, by these treatments (Fearn and La Rue, 1991, Ethylene inhibitors restore nodulation to sym 5 mutants of *Pisum sativum* L. cv. Sparkle, Plant Physiology 96: 239–244). Similar results were found using active compound 2.3.1.1 and $Ag_2SO_4$ in E107 (brz), a further defect mutant of the pea variety Sparkle (Guinel and La Rue, Ethylene inhibitors partly restore nodulation to pea mutant E107 (brz), Plant Physiology 99: 515–518).

In the case of the pea variety Sparkle, increased ethylene formation and, as a presumable result thereof, severely reduced nodule formation can be induced by provision of light in the root area. $Ag_2SO_4$ can reverse the reduced nodule formation by light (Lee and La Rue, Ethylene as a possible mediator of light- and nitrate-induced inhibition of nodulation of *Pisum sativum* L. cv Sparkle, Plant Physiology 100: 1334–1338).

Artificial treatment with 0.07 $\mu l/l$ of ethylene gas/l of air leads in the case of the pea varieties Sparkle and Rondo as well as in the case of white sweetclover (*Melilotus alba*) to a severe reduction in nodule formation. In the case of soybean plants, on the other hand, no significant effect on nodulation was detected even in the case of distinctly higher ethylene administration. In the case of peas (Sparkle), normal nodule formation could be restored by $Ag_2SO_4$ in the presence of ethylene (Lee and La Rue, Exogenous ethylene inhibits nodulation of *Pisum sativum* L. cv Sparkle, Plant Physiology 100: 1759–1763).

In the presence of certain Rhizobia strains, the common vetch *Vicia sativa* (subspecies *nigra*) forms only a small number of root nodules. Normal nodulation can be achieved here by application of 2.3.1.1 (Zaat et al., 1989, The ethylene inhibitor aminoethoxyvinylglycine restores normal nodulation by *Rhizobium leguminosarum biovar. viciae* on *Vicia sativa* subsp. nigra by suppressing the "Thick and short roots" phenotype, Planta 177: 141–150).

Peters and Crist-Estes (Nodule formation is stimulated by the ethylene inhibitor aminoethoxyvinylglycine, Plant Physiology 91: 690–693) were indeed able to increase the number of nodules formed by 2.3.1.1 in soilless cultures of lucerne (*Medicago sativa*), but no increase in fixation of $N_2$ and consequently also no improvement in growth resulted from this.

On the whole, the present findings do not indicate that it is possible to achieve increases in yield by the use of substances as in the above items 2. and 3. in legumes and other plant species under practical conditions. Surprisingly, however, it has now been found that the substances or substance classes listed in item 2 are suitable, in particular, for practical use. It is essential to the invention here that the compositions according to the invention are employed to reduce the ethylene content in the root zone of the soil and thus to achieve a soil improvement. The fact that bacteria, yeasts, fungi and Actinomycetes—among them also typical soil microorganisms—are able to produce ethylene is known. Microbial biosynthesis, however, obviously takes place differently than in higher plants (Fukuda and Ogawa, Microbial ethylene production, in: The Plant Hormone Ethylene, Mattoo, A. K. and Suttle, J. C. (eds.), CRC Press, Boca Raton, 1991, pp. 279–292). Also in this respect it was not to be expected that, for example, inhibititors of ethylene biosynthesis in higher plants would have an effect on the formation of ethylene in the soil.

According to the invention, three classes of substances are to be used for soil improvement or increased assimilation of nitrogen from the air, namely a) ethylene-binding compounds, eg. as listed in item 2.2;

b) inhibitors of the conversion of S-adenosyl-L-methionine to 1-aminocyclopropane-1-carboxylic acid, eg. as mentioned in item 2.3.1, in particular aminoethoxyvinylglycine, aminooxyacetic acid and oxime ethers of acetic acid or acid derivatives or salts thereof which form the free acid by hydrolysis or neutralization or oxime ethers of alkoxycarbonylmethyl acetates or acid derivatives or salts thereof which form the carboxymethyl acetate by hydrolysis or neutralization; and c) inhibitors of the conversion of 1-aminocyclopropane-1-carboxylic acid to ethylene, eg. as mentioned in item 2.3.2, in particular the active compounds 2.3.2.1–2.3.2.11.

Oxime ethers such as mentioned above are particularly preferred for reducing microbially produced ethylene and for increasing the $N_2$ assimilation of crop plants, in particular legumes. These compounds have the following common structural unit:

In this unit, the radicals on the C atom or on the oxygen can be very widely varied and in addition to hydrogen are customary organocarbon radicals such as alkyl, alkenyl, cycloalkyl, phenyl or benzyl radicals. For example, compounds of the formula I $$R^1R^2C=NO-CH_2-COOR^3 \qquad I,$$

may be mentioned, where $R^1$ and $R^2$ independently of one another are hydrogen or $C_1$–$C_6$-alkyl, $C_1$–$C_6$-haloalkyl, $C_1$–$C_4$-alkoxy-$C_1$–$C_6$-alkyl, $C_3$–$C_6$-alkenyl, unsubstituted or substituted phenyl having up to three substituents selected from: nitro, chlorine, fluorine, $C_1$–$C_3$-alkyl, $C_1$–$C_3$-haloalkyl and methylenedioxy, or $R^1$ and $R^2$, together with the carbon atom to which they are bonded, form a 5–7-membered ring which in turn can carry one or two $C_1$–$C_3$-alkyl groups, and $R^3$ is hydrogen, an agriculturally tolerable cation, $C_1$–$C_8$-alkyl, $C_3$–$C_7$-cycloalkyl, $C_1$–$C_4$-alkoxy-$C_1$–$C_6$-alkyl or a group $CH_2$—$C(O)$—$OR^4$, $R^4$ being $C_1$–$C_8$-alkyl, $C_3$–$C_7$-cycloalkyl, $C_1$–$C_4$-alkoxy-$C_1$–$C_6$-alkyl, hydrogen or an agriculturally tolerable cation.

Instead of the free acids, their environmentally tolerable salts can also be present, where the type of salt in general does not matter. Customarily the salts of those bases which do not adversely affect the action of I are suitable.

Particularly suitable basic salts are those of the alkali metals, preferably the sodium and potassium salts, those of the alkaline earth metals, preferably calcium, magnesium, copper, zinc and iron salts, and the ammonium salts, which can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl-(2-hydroxyethyl)ammonium salts, the phosphonium salts and the sulfonium salts, preferably tri-$(C_1$–$C_4)$-alkylsulfoxonium salts.

Of particular interest for application according to the invention are the following combinations of radicals:

$R^1$ and $R^2$: $C_1$–$C_6$-alkyl, eg. methyl, ethyl, propyl or $R^1$ and $R^2$, together with the carbon to which they are bonded, form a 5–7-membered ring, eg. cyclopentylidene or cyclohexylidene, $R^3$: hydrogen, $C_1$–$C_6$-alkyl or a $CH_2$—$C(O)OR^4$ group $R^4$: hydrogen or $C_1$–$C_6$-alkyl, and the compounds Nos. 2.3.1.3–2.3.1.6.

| No. | Structure |
|---|---|
| 2.3.1.3 |  $(CH_3)_2C=N-O-CH_2-C(O)-O-CH_2-COOCH_3$ |
| 2.3.1.4 | $(CH_3)_2C=N-O-CH_2-C(O)-O-(CH_2)_5CH_3$ |
| 2.3.1.5 | $C_6H_{11}-C(=N-O-CH_2-C(O)-O-CH_2-O-CH(CH_3)_2)$ |
| 2.3.1.6 | $(CH_3)_2C=N-O-CH_2-C(O)-OH$ | and the acids on which they are based and alkali metal, alkaline earth metal or ammonium salts thereof.

European Applications EP-A 501 326 and EP-A 243 834 describe the preparation of the compounds I and their bioregulatory action or they can be prepared in an analogous manner.

The active compounds can be brought into the part of the soil relevant for plant growth in varying preparations in various ways. It is not to be excluded here that a part of the amount of active compound employed in each case is absorbed by the higher plant itself. The positive action resulting for growth and yield is low, however, in comparison with the soil-improving effect.

The following application processes have specifically proven suitable, without this listing being a claim to completeness:

I Spray Application of an Aqueous Active Compound Preparation to the Soil Surface The active compound is washed into the part of the soil covered by roots by the spray liquid and by natural precipitation or by artificial irrigation. The amount of water necessary for this is very variable, depending on the soil type, the soil moisture present and the plant species cultivated, but can easily be determined by the user. In a pre-sowing soil treatment, the active compound can also be incorporated into the soil by extensive tilling. In a pre-emergence or post-mergence application, tilling of this type can also be carried out between the seed rows or between the rows of the still-young plants.

II Application of Active Compound Granules to the Soil Surface

The granules can be applied using field broadcasters, or alternatively by aircraft. The last-mentioned process is particularly advantageous if older plant populations are to be treated. The introduction of the active compound into the soil is carried out by analogy following the methods mentioned in I.

III Application with the Irrigation Water

The active compounds according to the invention can be applied using customary sprinkler irrigation plants and droplet watering plants (analogously to a "fertigation").

IV Underground Application

Aqueous preparations of the compositions according to the invention can also be injected directly into the rooted part of the soil using appropriate equipment.

V Application with the Sowing Operation

Application to the seed has also proven particularly practical. Here, on the one hand, aqueous active compound preparations can be sprayed into the seed furrow during sowing or granules can be additionally drilled into the seed furrow. Application as a seed treatment is also highly practicable, especially as here it is ensured that the active compound reaches the immediate root area of the plant.

Depending on the plant species, soil type, application date, type of application, weather conditions and active compound used, the application rates of the active compounds according to the invention can vary greatly:

In the types of application I to IV the application rates are in general from 1.0 to 10,000 g/ha, preferably from 10 to 1,000 g/ha, of active compound. Spray or granule applications in the seed furrow in general require from 0.5 to 5,000 g/ha, preferably from 5 to 500 g/ha, of active compound.

When applied with the seed, favorable results are obtained with application rates of from 1 to 10,000 mg/kg, preferably from 10 to 1,000 mg/kg, of active compound.

In the case of the types of application I to IV, the active compounds according to the invention can be applied, either once or divided into several doses, in the required amounts.

Examples of formulations are:

I 20 parts by weight of the active compound 2.3.1.3 are well mixed in 3 parts by weight of the sodium salt of diisobutylnaphthalenesulfonic acid, 17 parts by weight of the sodium salt of a lignosulfonic acid from a sulfite waste liquor and 60 parts by weight of powdered silica gel and ground in a hammer mill. A spray liquor which contains 0.1% of the active compound is obtained by finely dispersing the mixture in 20,000 parts by weight of water.

II 3 parts by weight of the active compound 2.3.1.3 are intimately mixed with 97 parts by weight of finely divided kaolin. In this manner, a dust is obtained which contains 3% by weight of the active compound.

III 30 parts by weight of the active compound 2.3.1.4 are intimately mixed with a mixture of 92 parts by weight of powdered silica gel and 8 parts by weight of liquid paraffin which has been sprayed onto the surface of this silica gel. In this manner a preparation of the active compound having good adhesiveness is obtained.

IV 40 parts by weight of the active compound 2.3.1.6 are intimately mixed with 10 parts of sodium salt of a phenolsulfonic acid/urea/formaldehyde condensate, 2 parts of silica gel and 48 parts of water. A stable aqueous dispersion is obtained. By diluting with 100,000 parts by weight of water, an aqueous dispersion is obtained which contains 0.04% by weight of active compound.

V 20 parts by weight of the active compound 2.3.1.5 are intimately mixed with 2 parts of calcium salt of dodecylbenzenesulfonic acid, 8 parts of fatty alcohol polyglycol ether, 2 parts of sodium salt of a phenolsulfonic acid/urea/formaldehyde condensate and 68 parts of a paraffinic mineral oil. A stable oily dispersion is obtained.

VI 90 parts by weight of the active compound 2.3.1.3 are mixed with 10 parts by weight of N-methyl-alpha-pyrrolidone and a solution is obtained which is suitable for application in the form of very small drops.

VII 20 parts by weight of the active compound 2.3.1.6 are dissolved in a mixture which consists of 80 parts by weight of xylene, 10 parts by weight of the addition product of from 8 to 10 mol of ethylene oxide to 1 mol of oleic acid-N-mono-ethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water, an aqueous dispersion is obtained which contains 0.02% by weight of the active compound.

VIII 20 parts by weight of the active compound 2.3.1.3 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

IX 20 parts by weight of the active compound 2.3.1.4 are dissolved in a mixture which consists of 25 parts by weight of cyclohexanol, 65 parts by weight of a mineral oil fraction of boiling point from 210 to 280° C. and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

X 1 part by weight of the active compound 2.3.1.3 is nozzled as a 25% strength solution in methyl oleate onto 96 parts by weight of finely disperse calcium sulfate carrier. Broadcastable granules having an active compound content of 1% are thus obtained.

XI 3 parts by weight of the active compound 2.3.1.3, 15 parts by weight of sodium salt of a phenolsulfonic acid/urea/formaldehyde condensate, 272 parts by weight of kaolin and 84 parts by weight of water are intimately mixed in a kneader. The mass obtained is shaped into granules by means of an extruder and then dried. Broadcastable granules having an active compound content of 1% are obtained.

XII For preparation of a microcapsule formulation, 250 parts of the active compound 2.3.1.3 together with 19 parts of sodium 2-acrylamidopropanesulfonate in 800 parts of water are slowly mixed with a 70% strength solution of 57 parts of a melamine/formaldehyde precondensate while stirring rapidly. The pH is kept at 5.5 during this process. After addition is complete stirring is continued for 1 h at 70° C. for curing. The capsule suspension thus obtained is converted by addition of thickener as well as dispersant and wetting agent into a storage-stable suspension concentrate which has an active compound content of 250 g/l and after diluting can be applied as a slow-release formulation.

XIII Slow-release fertilizer granules 3,800 g of a granulated PK fertilizer (eg. 8+15 (+6 MgO)) are heated to 45° C. in a fluidized bed apparatus in the course of 10 minutes. Parallel to this, a mixture of 4 g of active compound and 112 g of an 18% strength aqueous polymer wax emulsion is prepared, which is described in greater detail eg. in EP-A-166 235. This mixture is then sprayed onto the warmed granules in the fluidized bed for 14 minutes (about 8 g/min) and dried. A further 1,000 g of the polymer wax emulsion are then nozzled on, the spray rate slowly being increased from initially 12 g/min up to 22 g/min. After spraying is complete, operation of the fluidized bed is continued until the waste air temperature is 45° C., then the heating is switched off and the fluidized bed is emptied after cooling to 30° C.

In these application forms, the compositions according to the invention can also be mixed with one another and can also be present together with other active compounds, such as eg. herbicides, insecticides, bioregulators, fungicides and bactericides. Mixtures with fertilizers can also be applied. In the case of legumes, a joint application with bacteria of the genera Rhizobium and Bradyrhizobium can also be carried out. As a result of mixing with certain bioregulators and fungicides (inhibitors of cytochrome P-450-dependent monooxygenases), synergistic effects also occur, ie. the activity of the combination product is greater than the added activities of the individual components.

BIOLOGICAL EXAMPLES

I Lack of Activity of the Compositions According to the Invention on the Growth of Soil Microorganisms In this test various compositions according to the invention were mixed into various soils at different application rates. After aerobic or anaerobic incubation at 20° C. for 3 days, samples were taken from the various batches and, to determine the number of microorganisms, were diluted and mixed into nutrient media (selective for bacteria or fungi). The inoculated nutrient media were incubated for a period of 4 days at 25° C. The number of microorganism colonies which were then to be observed was used to calculate the number of microorganisms in the various soil samples.

It was seen that the various compositions do not exert any effect on the growth of the soil microorganisms. A reduced ethylene formation of the soil can therefore not be attributed to a fungicidal or bactericidal effect of the compositions. At the same time, it can be expected from these results that the compositions according to the invention have no adverse effects on the microorganisms important for soil fertility.

II Inhibition of Microbial Ethylene Formation in the Soil

In these experiments a non-sterile soil was used such as occurs naturally in Limburgerhof, Federal Republic of Germany. The soil characteristics are as follows:

loamy sand
18% separable parts of <0.02 mm
pH 6.1
humus content 1.2%
maximum water capacity 36%
cation exchange capacity 4.8 meq/100 g 25 g of air-dried soil were in each case mixed with an aqueous active compound solution, adjusted to a determined percentage of the maximum water capacity by addition of further water and then incubated in the dark at 25° C. for a period of two to four days in a closed airtight 50 ml vessel. The amount of ethylene formed during this period was detected by gas chromatography.

Figure 1:
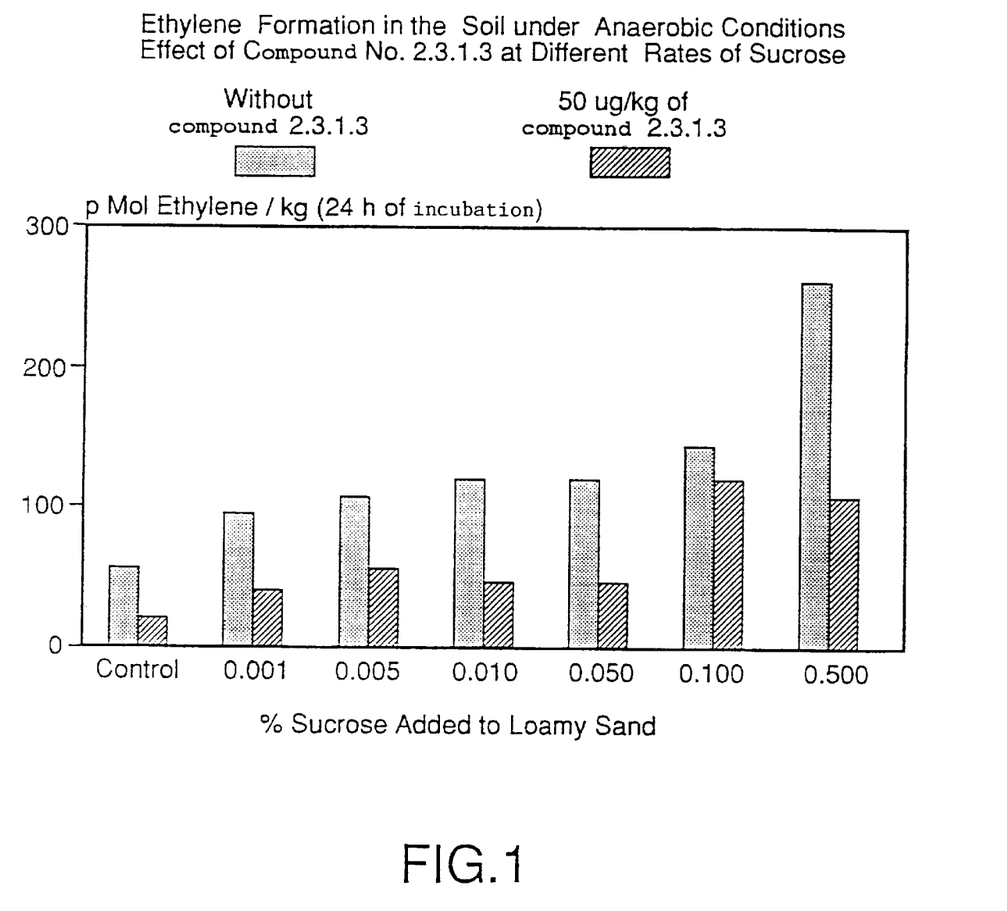
FIG. 1 shows ethylene formation in the soil under an aerobic conditions and the effect of compound 2.3.1.3 at different rates of sucrose.

For simpler detection of the microbially formed ethylene, it has proven useful to add to the soil sample a small amount of carbohydrate (normally sucrose) in order in this way to stimulate the growth of the microorganisms and thus also their ethylene formation. FIG. 1 shows that ethylene production can be significantly increased by an admixture of sucrose of this type. Independently of the amount of sucrose employed, the active compound according to the invention reduces ethylene formation in nearly all cases by more than 50% at an application rate of 50 μg/kg of soil.

Figure 2:
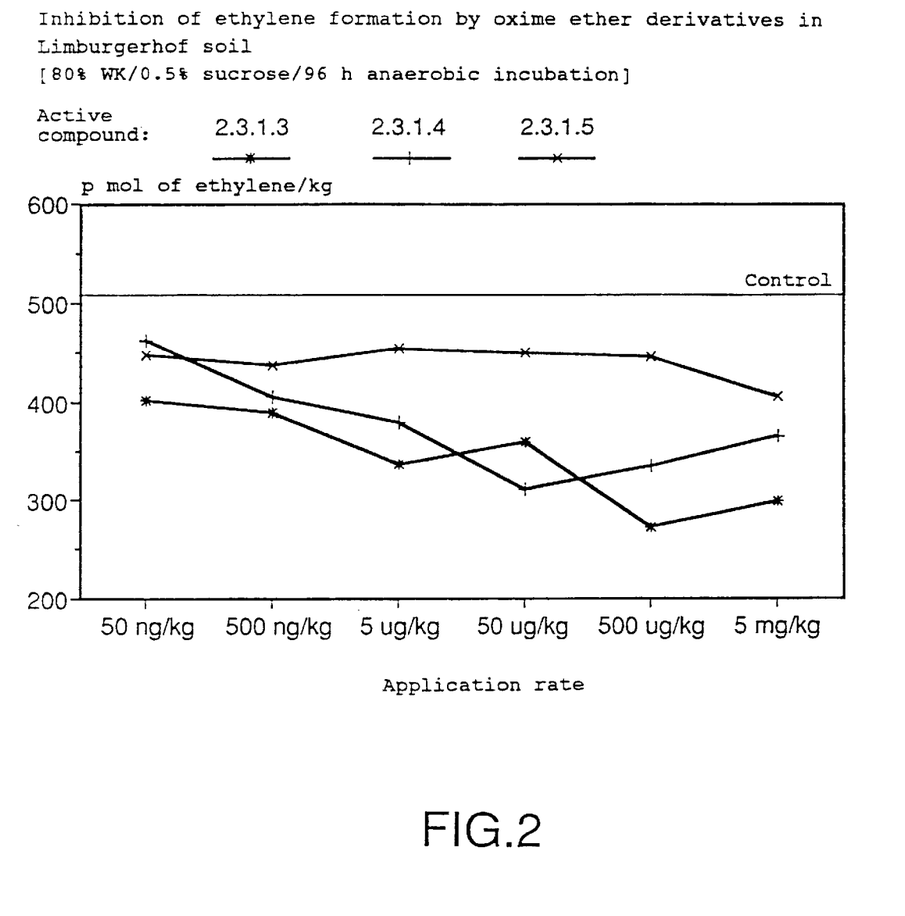
FIG. 2 shows inhibition of ethylene formation by oxime ether derivatives in Limburgerhoff soil.

The experiments which are part of FIG. 2 show that the oxime ether derivatives are biologically active over a very wide concentration range. Even application rates of 50 ng/kg of soil can still cause a clear inhibition of ethylene formation.

III Promotion of Growth in Various Plant Species (results from climatic chamber and greenhouse tests)

In these tests various types of non-sterile soils were used. The cultivation of the plants was carried out under greenhouse or climatic chamber conditions. The active compounds according to the invention were applied uniformly distributed over the soil surface in an aqueous preparation after the emergence of the respective test plants. The supply of water for the plants was carrried out using the same technique, always paying attention to uniform moistness of the soil. In the case of the cultivation of legumes, defined amounts of species-specific Rhizobia were admixed to the soil. In some cases inoculation was also carried out by seed treatment.

1. Promotion of Shoot Growth of Wheat and Rape

Wheat (Ralle) and rape (Petranova) plants were cultured under greenhouse conditions in low N Limburgerhof soil in plastic pots (500 ml) and watered from above as required. The water content of the soil here was about 80% of the maximum water capacity. A few days after emergence the plants were thinned out to 40 plants per pot.

10 days after sowing aqueous preparations of 2.3.1.3 were applied by watering to 8 pots per test series in each case. 16 pots in each case remained untreated. 3 weeks after treatment the fresh shoot weight of the plants was determined.

The results showed that shoot growth was promoted in nearly all cases.

2. Promotion of the Production of Shoot and Root Biomass, Formation of Root Nodules and Assimilation of Nitrogen in the Case of Peas (*Pisum sativum*).

a) Peas (Kleine Rheinländerin) were cultivated under greenhouse conditions in low N Limburgerhof soil in plastic pots (500 ml) and watered from above as required (a constant weight was maintained here). A few days after emergence the plants were thinned out to 5 plants per pot.

In four pots in each case aqueous active compound solutions of one concentration of 2.3.1.3 were applied by watering. Four pots remained untreated.

3 weeks after treatment the following results were obtained:

TABLE 1

| Application rate [mg/pot] | Dry matter* [g/pot] | Nodules [number/pot] | Total N** [mg/pot] |
|---|---|---|---|
| Control | 3.3 | 13 | 78.5 |
| 0.03 mg/pot | 3.2 | 28 | 75.0 |
| 0.30 mg/pot | 4.0 | 127 | 120.5 |
| 3.00 mg/pot | 3.1 | 99 | 109.5 |

\* = Dry matter in shoot + root
Total N** = total nitrogen in shoot + root b) Peas (Kleine Rheinländerin) were cultivated under greenhouse conditions in low N Limburgerhof soil in plastic pots (500 ml) and watered from above as required (constant weight). A few days after emergence the plants were thinned out to 5 plants per pot.

In four pots in each case aqueous active compound solutions of one concentration of 2.3.1.3 were applied by watering. Four pots remained untreated.

12 days after treatment the following results were obtained:

TABLE 2

| Application rate [mg/pot] | Dry matter* [g/pot] | Nodules [number/pot] |
|---|---|---|
| control | 2.55 | 20 |
| 0.001 | 2.65 | 31 |
| 0.003 | 3.07 | 68 |

TABLE 2-continued

| Application rate [mg/pot] | Dry matter* [g/pot] | Nodules [number/pot] |
|---|---|---|
| 0.010 | 3.00 | 66 |
| 0.030** | 2.32 | 30 |
| 0.100 | 2.52 | 59 |
| 0.300 | 3.13 | 76 |

*Shoot + root
**Insect attack c) Peas (Field Peas VNS) were cultivated under greenhouse conditions in low N, sandy loam soil in plastic pots (750 ml) and watered from above as required. A few days after emergence the plants were thinned out to 7 plants per pot.

In 5 pots in each case 25 ml each of an aqueous preparation of one concentration of 2.3.1.3 were applied by watering. 5 pots remained untreated.

30 days after treatment the following results were obtained:

TABLE 3

| Application rate [g of a.s./ha] | Nodules [number/plant] | Dry matter root [mg/plant] | Dry matter shoot [mg/plant] |
|---|---|---|---|
| — | 6.1 | 275 | 459 |
| 3 | 41.5 | 849 | 1064 |
| 30 | 39.4 | 704 | 795 |
| 300 | 56.1 | 945 | 1209 |

The results confirmed using peas as test plants show that growth can be clearly improved using the compositions according to the invention. This also allows an increase in the yield capacity of peas to be expected.

Obviously the improved growth is primarily to be attributed to increased nodulation and, associated therewith, increased assimilation of $N_2$ from the air.

3. Promotion of the Production of Shoot and Root Biomass as Well as of Root Nodule Formation in Soybeans (*Glycine max*)

a) Soybean plants (Delta Pine 415) were cultivated under greenhouse conditions in low N Limburgerhof soil in plastic pots (500 ml) and watered from above as required. A few days after emergence the plants were thinned out to 5 plants per pot.

In 8 pots in each case per test member an aqueous active compound solution of 2.3.1.3 was applied by watering. 16 pots remained untreated in each case.

After 3 weeks the following results were obtained:

TABLE 4

| Application rate [mg of a.s./pot] | Nodules [number/pot] | Total N* [% of control] |
|---|---|---|
| — | 49 | 100 |
| 0.003 | 60 | 109 |
| 0.030 | 62 | 108 |
| 0.300 | 73 | 118 |

*shoot + root b) Test procedure as in 3 a) active compound 2.3.1.3

TABLE 5

| Application rate [mg of a.s./pot] | Nodules [number/pot] |
|---|---|
| — | 47 |
| 0.003 | 72 |
| 0.030 | 83 |
| 0.300 | 69 | c) Test procedure as in 3 a)

TABLE 6

| Active compound | Application rate [mg of a.s./pot] | Nodules [number/pot] | Total N* [% of control] |
|---|---|---|---|
| — | — | 46 | 100 |
| 2.3.1.4 | 0.030 | 55 | 103 |
| 2.3.1.4 | 0.300 | 66 | 110 |
| 2.3.1.5 | 0.030 | 70 | 104 |
| 2.3.1.5 | 0.300 | 61 | 107 |

*shoots + root d) Soybeans (A 5403) were cultivated under greenhouse conditions in low N, sandy loam soil in plastic pots (750 ml) and watered from above as required. A few days after emergence the plants were thinned out to 3 plants per pot.

In 5 pots in each case 25 ml each of an aqueous preparation of one concentration of 2.3.1.3 were applied by watering. 5 pots remained untreated.

30 days after treatment the following results were obtained:

TABLE 7

| Application rate [g of a.s./ha] | Nodules [number/plant] | Dry matter root [mg/plant] | Dry matter shoot [mg/plant] |
|---|---|---|---|
| — | 38.3 | 1955 | 3616 |
| 3 | 47.6 | 2806 | 4020 |
| 300 | 54.9 | 1326 | 4117 |

An improvement in the seed yield of soybeans as a result of the compositions according to the invention can be expected from the test results.

4. Promotion of the Production of Shoot and Root Biomass as Well as of Root Nodule Formation in Field Beans (*Vicia faba*).

Bean plants (Small Seeded Bell) were cultivated under greenhouse conditions in low N, sandy loam soil in plastic pots (750 ml) and watered from above as required. A few days after emergence the plants were thinned out to 3 plants per pot.

In 5 pots in each case 25 ml each of an aqueous preparation of one concentration of 2.3.1.3 were applied by watering. 5 pots remained untreated.

25 days after treatment the following results were obtained:

TABLE 8

| Application rate [g of a.s./ha] | Nodules [number/plant] | Dry matter root [mg/plant] | Dry matter shoot [mg/plant] |
| --- | --- | --- | --- |
| — | 30.9 | 1090 | 2310 |
| 30 | 34.3 | 1380 | 2880 |
| 300 | 50.7 | 1470 | 3940 |
| 3000 | 48.2 | 960 | 2450 |

It is shown by the results that, even in the case of beans, increases in yields of seeds are to be expected as a result of the compositions according to the invention.

5. Promotion of the Production of Shoot and Root Biomass as Well as of the Formation of Root Nodules in Chick-peas (*Cicer arietinum*)

Chick-pea plants (UC-27) were cultivated under greenhouse conditions in low N, sandy loam soil in plastic pots (750 ml) and watered from above as required. A few days after emergence the plants were thinned out to 3 plants per pot.

In 6 pots in each case 25 ml each of an aqueous preparation of one concentration of 2.3.1.3 were applied by watering. 6 pots remained untreated.

25 days after treatment the following results were obtained:

TABLE 9

| Application rate [g of a.s./ha] | Nodules [number/plant] | Dry matter root [mg/plant] | Dry matter shoot [mg/plant] |
| --- | --- | --- | --- |
| — | 11.3 | 1100 | 2110 |
| 30 | 31.4 | 1280 | 2690 |
| 300 | 44.0 | 1520 | 3350 |
| 3000 | 6.2 | 1150 | 4110 |

It is to be expected that the compositions according to the invention lead to increases in seed yields in the case of chick-peas. However, the results also show that additional formation of shoot and root biomass is not unconditionally associated with increased formation of root nodules.

6. Promotion of the Production of Shoot Biomass in the Case of Lucerne (*Medicago sativa*)

Lucerne plants (Maricopa) were cultivated under greenhouse conditions in low N, sandy loam soil in plastic pots (750 ml) and watered from above as required. A few days after emergence the plants were thinned out to 3 plants per pot.

In 5 pots in each case 25 ml of an aqueous preparation of one concentration of 2.3.1.3 were applied by watering. 5 pots remained untreated.

25 days after treatment the following results were obtained:

TABLE 10

| Application rate [g of a.s./ha] | Root nodules [number/plant] | Dry matter shoot [mg/plant] |
| --- | --- | --- |
| — | 10.5 | 180 |
| 30 | 10.7 | 300 |
| 300 | 10.3 | 240 |

The results show that the compositions according to the invention promote the production of shoot biomass in lucerne. It is also obvious that this stimulation is not associated with increased formation of root nodules.

IV Results of Field Tests Under Practical Conditions

The tests a) and b) were carried out under conditions like those in practice in 1993 on the field test site of BASF Corporation in Holly Springs, N.C., USA. This location is distinguished by a medium-heavy soil (sandy loam).

a) Promotion of the seed yield in soybeans (*Glycine max*)

Soybeans of the variety Delta Pine 147 were used. Treatment was carried out to the following stages of development: 11 (1st trefoil formed), 13 (3rd trefoil formed) and 14 (5th trefoil formed). For treatment, the soil between the rows was sprayed with an aqueous preparation of the active compound 2.3.1.3. Immediately after the application, the active compound was washed into the soil by spray irrigation with 20 mm of water. The spray irrigation was also used to wash off active compound which had possibly reached the leaves.

Harvesting of the plants at full maturity gave the following results:

TABLE 11

| Active compound 2.3.1.3 [g/ha of a.s.] | Growth stage during treatment | Bean yield [dt/ha] | [%] |
| --- | --- | --- | --- |
| 0 | — | 29.9 | 100 |
| 10 | 11 | | 104 |
| 100 | 11 | | 122 |
| 1000 | 11 | | 110 |
| 10 | 13 | | 116 |
| 100 | 13 | | 117 |
| 1000 | 13 | | 122 |
| 10 | 14 | | 110 |
| 100 | 14 | | 112 |
| 1000 | 14 | | 108 | b) Promotion of the seed yield and of the seed quality in groundnuts (*Arachis hypogaea*)

Groundnuts of the variety Florigiant were used. Treatment was carried out 20, 27 and 34 days after emergence of the plants. For treatment, the soil between the rows was sprayed with an aqueous preparation of the active compound 2.3.1.3. Immediately after application the active compound was washed into the soil by spray irrigation with 20 mm of water. The spray irrigation was also used to wash off active compound which had possibly reached the leaves.

Harvesting of the plants at full maturity gave the following results:

TABLE 12

| Active compound 2.3.1.3 [g/ha of a.s.] | Treatment date | Yield of groundnuts dt/ha | % | Seeds of the highest quality level % |
| --- | --- | --- | --- | --- |
| 0 | — | 45.4 | 100 | 38.0 | 100 |
| 10 | 20 days after emergence | | 108 | | 124 |
| 100 | | | 121 | | 95 |
| 1000 | | | 113 | | 103 |
| 10 | 27 days after emergence | | 109 | | 121 |
| 100 | | | 104 | | 113 |
| 1000 | | | 120 | | 113 |
| 10 | 34 days | | 124 | | 113 |

TABLE 12-continued

| Active compound 2.3.1.3 [g/ha of a.s.] | Treatment date | Yield of groundnuts | | Seeds of the highest quality level |
|---|---|---|---|---|
| | | dt/ha | % | % |
| 100 | after emergence | 121 | | 84 |
| 1000 | | 113 | | 108 |

The results for a) and b) make the yield-promoting action of the compositions according to the invention clear. In the test with groundnuts it is furthermore shown that the soil-improving action of the compositions also results in an improved quality of the harvested crops.

We claim:

1. A process for increasing the assimilation of nitrogen by higher plants, which comprises supplying compounds to the soil zone relevant for root growth which bind ethylene or in higher plants inhibit ethylene biosynthesis between S-adenosyl-L-methionine and 1-aminocyclopropane-1-carboxylic acid or 1-aminocyclopropane-1-carboxylic acid and ethylene respectively.

2. A process as claimed in claim 1, wherein the plants are legumes.

* * * * *